United States Patent [19]
Strong

[11] 4,354,032
[45] Oct. 12, 1982

[54] ALKYL N-3-HALO-,N-3,5-DIHALOBENZOYL-N-ISO-PROPYLAMINOACETATE HERBICIDES

[75] Inventor: Walker A. Strong, Hudson, Ohio

[73] Assignee: PPG Industries, Inc., Pittsburgh, Pa.

[21] Appl. No.: 931,705

[22] Filed: Aug. 7, 1978

[51] Int. Cl.³ .............................................. C07C 101/10
[52] U.S. Cl. .......................................... 560/41; 71/111
[58] Field of Search ...................... 71/111; 560/19, 41; 260/471 A

[56] References Cited

U.S. PATENT DOCUMENTS 3,465,081  9/1969  Fuhlhage .......................... 424/309

FOREIGN PATENT DOCUMENTS 49-11415  3/1974  Japan .

Primary Examiner—Catherine L. Mills
Attorney, Agent, or Firm—Edward J. Whitfield; Robert J. Grassi

[57] ABSTRACT

Disclosed are novel herbicides, such as ethyl N-3,5-dichlorobenzoyl-N-isopropylaminoacetate, as well as their use against weeds.

8 Claims, No Drawings

ALKYL N-3-HALO-,N-3,5-DIHALOBENZOYL-N-ISO-PROPYLAMINOACETATE HERBICIDES

BACKGROUND OF THE INVENTION

1. Field of the Invention

This invention relates to alkyl N-3-halo-, and N-3,5-dihalobenzoyl-N-isopropylaminoacetate compounds and their use as herbicides.

2. Description of the Prior Art

U.S. Pat. No. 3,877,925 describes N-benzyl-N-isopropyl-3,5-dichloro-, 3-chloro-, or 3,5-dimethylthiobenzamide as preemergent weed controllers. U.S. Pat. No. 3,880,903 describes 3-, 5-, N-substituted benzamides, such as N-(1-cyanoisopropyl)-3,5-dichlorobenzamides as herbicides. U.S. Pat. No. 3,941,783 describes a process for forming N,N-disubstituted carboxylic amides, such as 3,4-dichlorobenzoic diisobutylamides, used for tranquillizing agents or plant protective agents. U.S. Pat. No. 3,187,042 describes N-alkoxy benzamides; such as N-methoxy-N-methyl-2,3,5-tri-chlorobenzamide used as postemergent herbicides. U.S. Pat. No. 3,042,715 describes polyiodated benzamides; such as N-(3-amino-2,4,5,6-tetraiodobenzoyl)-N-isopropylamino-propionic acid used for X-ray absorption. U.S. Pat. No. 3,661,991 describes N-(1,1-dialkyl-3-chloroacetonyl benzamides); such as N-(1,1-dimethyl-3-chloroacetonyl)-3-chlorobenzamides used as selective herbicides and fungicides. U.S. Pat. No. 3,707,366 discloses benzamides; such as N-benzyl-N-isopropyl-3-bromobenzamides used as herbicides. U.S. Pat. No. 4,021,224 discloses antidotes of N,N-disubstituted carboxylic amides such as N-methyl-N-propargyl-2-iodobenzoylamides used to prevent herbicides from harming platns. None of the prior art teaches or suggests that the compositions described herein are suitable for control of weeds, and particularly those weeds described herein.

SUMMARY OF THE INVENTION

The invention is to herbicidally useful alkyl N-3,5-dihalobenzoyl-N-isopropylaminoacetate compounds graphically represented by the general formula:

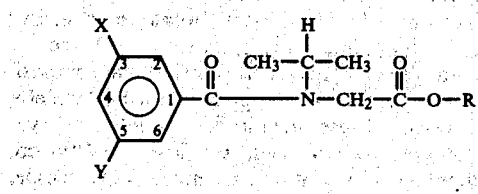

wherein:
X is chlorine, bromine;
Y is hydrogen, fluorine, chlorine, bromine, or iodine; and
R is an alkyl of up to four carbon atoms.
The compounds are useful against weeds; for example, ethyl N-3,5-dichlorobenzoyl-N-isopropylaminoacetate is especially useful against weeds.

DESCRIPTION OF THE PREFERRED EMBODIMENTS

The novel herbicidally useful alkyl N-3,5-dihalobenzoyl-N-isopropylaminoacetate compounds contemplated herein are graphically represented by the general formula:

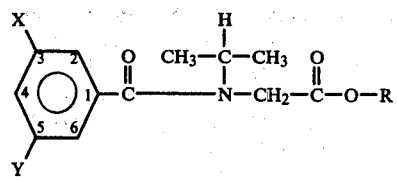

wherein:
X is fluorine, chlorine, bromine, or iodine;
Y is hydrogen, chlorine, bromine; and
R is an alkyl of up to four carbon atoms or an alkoxy alkyl of up to four carbon atoms.

Note, as used herein and in the claims, the terms "compound" and "composition" are used interchangeably.

As used herein and in the claims, the phrase "an alkyl of up to four carbon atoms" refers to: methyl, ethyl, n-propyl, isopropyl, n-butyl, isobutyl, sec-butyl, or tert-butyl.

The preferred alkyls are methyl, ethyl, n-propyl and isopropyl, and the most preferred alkyl is ethyl.

As used herein and in the claims, the phrase "an alkoxyalkyl of up to four carbon atoms" refers to: 2-methoxyethyl, 3-methoxypropyl, 2-methoxypropyl, 2-methoxy-1-methylethyl, and 2-ethoxyethyl.

The preferred alkoxyalkyls are: 2-methoxyethyl, 2-methoxypropyl, and 2-methoxy-1-methylethyl, and the most preferred alkoxyalkyl is 2-methoxyethyl.

Examples of compounds encompassed by the general formula are:

a. Those in which R is an alkyl mentioned herein and X and Y are as mentioned herein, such as:
methyl N-(3,5-diiodobenzoyl)-N-isopropylaminoacetate;
ethyl N-(3-chlorobenzoyl)-N-isopropylaminoacetate;
methyl N-(3-bromobenzoyl)-N-isopropylaminoacetate;
n-butyl N-(3,5-dibromobenzoyl)-N-isopropylaminoacetate;
isobutyl N-(3-bromo-5-chlorobenzoyl)-N-isopropylaminoacetate;
methyl N-(3,5-dichlorobenzoyl)-N-isopropylaminoacetate.

Although all of the compounds encompassed by the general formula are useful as described herein, some are more preferred than others.

The compounds in which R is one of the preferred alkyls mentioned herein are preferred, and the compounds in which R is ethyl are particularly preferred.

Of the compounds encompassed herein by the general formula, those in which Y is hydrogen are generally useful. Those compounds in which X and Y are bromine are preferred, and those compounds in which X is bromine and Y is chlorine are highly preferred. Those compounds in which X and Y are chlorine are especially preferred.

The most preferred compound is ethyl N-(3,5-dichlorobenzoyl)-N-isopropylaminoacetate.

SYNTHESIS OF THE COMPOUNDS

Those compounds in which R is an alkyl of from one to four carbon atoms or an alkoxyalkyl mentioned herein are made by esterifying the bromoacetic acid or chloroacetic acid so as to form, for example, ethyl bromoacetate, which is then reacted with isopropylamine under the appropriate conditions to form the N-isopropylaminoacetate. The N-isopropylaminoacetate is reacted with the 3,5-dihalobenzoylchloride so as to form the corresponding alkyl ester, such as ethyl N-3,5-dichlorobenzoyl-N-isopropylaminoacetate.

The following Example illustrates the synthesis of the compounds mentioned herein.

EXAMPLE I

Synthesis of Ethyl N-(3,5-dichlorobenzoyl)-N-isopropylaminoacetate a. Synthesis of Ethyl N-isopropylaminoacetate The procedure followed is generally described in *The Journal of Pharmaceutical Sciences*, 51, (1962), pages 1058-1061 and Speziale, A. J. and Jaworski, W., *Journal of Organic Chemistry*, 25, pp. 728-732 (1960).

A 300 milliliter round-bottom, 3-neck flask was equipped with a condenser, a thermometer, a dropping funnel, and a Teflon ® spin-bar magnet for stirring. The outlets were protected from moisture by calcium chloride drying tubes and the flask was immersed in an ice-salt cooling mixture.

The flask was charged with 100 milliliters of diethyl ether solution containing isopropylamine (0.4 mole, 23.6 grams) and the solution was stirred until cooled below 0° C. Then 30 milliliters of diethyl ether solution containing ethyl bromoacetate (0.2 mole, 32.4 grams) was added dropwise with stirring over a period of about 2 to 3 hours, followed by continued stirring as the cooling bath warmed to room temperature. The reaction mixture was allowed to stand overnight.

The reaction mixture was filtered by suction and the white crystalline solid of the isopropylamine hydrobromide salt was removed by collecting it on a sintered glass funnel. To extract any retained ethyl N-isopropylaminoacetate from the hydrobromide salt, the hydrobromide salt was slurried with solvent and refiltered.

The filtrate containing the ethyl N-isopropylaminoacetate was charged to a rotary evaporator and the solvent was removed under reduced pressure, and the concentrated liquid was distilled under reduced pressure and the fractions were collected to give 21.8 grams (75 percent yield) of a liquid with a boiling point of 65°-72° C. at 20 mm pressure, $n_D^{20}1.4170-1.4180$, assaying 98.3 percent (Gas chromatography area percentage).

b. Synthesis of Ethyl N-3,5-dichlorobenzoyl-N-isopropylaminoacetate

The procedure was an adaptation of the preparations described by Modi et al, *Journal of Organic Chemistry*, 35, page 228 (1970).

A 250 milliliter round-bottom, 3-neck flask was equipped with a condenser, a thermometer, a dropping funnel, and a Teflon ® spin-bar magnet for stirring. The outlets were protected from moisture by calcium chloride drying tubes, and the flask was immersed in an ice-water cooling mixture. The flask was charged with an 80 milliliter dichloromethane solution containing 0.015 mole (2.2 grams) of the ethyl N-isopropylaminoacetate (described above) and 0.015 mole (1.5 grams) of triethylamine. The solution was stirred while cooling in an ice-water bath. A 20 milliliter solution of dichloromethane containing 0.015 mole (3.14 grams) of 3,5-dichlorobenzoylchloride was added dropwise over a period of 1.0 hour with stirring and the stirring was continued for several hours followed by allowing the mixture to warm to room temperature. The reaction solution was washed four times with water (25 milliliters) to remove the triethylamine hydrochloride. The washed organic solution was filtered to remove the phase water and concentrated first by rotary evaporation (house vacuum, water bath to 65° C.) to 4.9 grams of a dull yellow syrup ($n_D^{20}1.5257$) and then, using a vacuum pump (<1 mm, oil bath to 50° to 60° C.) for 1.0 hour, to 4.5 grams (94 percent crude yield) $n_D^{20}(1.5280)$ ethyl N-3,5-dichlorobenzoyl-N-isopropylaminoacetate. It had a mass spectra (m/e) of molecular weight of 317, an infrared spectra (neat) mull technique with ester C=O band at 1745 centimeters$^{-1}$ and amide (C=O) band at 1635 centimeters$^{-1}$. It had the following nuclear magnetic resonance values δ (CDCl$_3$) of 1.1 (doublet, 6H, (CH$_3$)$_2$C—), 1.3 (triplet, 3H, CH$_3$—), 3.7-4.5 (4.0 broad singlet, 4.2 quartet, (overlap), 5H, CH$_2$N, CH$_2$, CH (heptet obscured)), and 7.3-7.5 (multiplets, 3H, aromatic).

Applications of the Compositions Against Weeds

The new compounds of this invention are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area, and the like. Thus, while the application of up to only about one or two ounces of active compound per acre may be sufficient for good control of a light infestation of weeds growing under adverse conditions, the application of 2 pounds or 12 pounds or more of an active compound per acre may be required for good control of a dense infestation of hardy perennial weeds growing under favorable conditions.

a. Examples Of Weeds Which May Be Controlled By The Compounds Described Herein

Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds which may be controlled by the compositions set forth herein, when applied in a herbicidally effective amount. These include field pennycress, ryegrass, goosegrass, chickweed, purslane, smartweed, knotweed, wild buckwheat, kochia, medic, corn cockle, ragweed, sow-thistle, croton, cuphea, dodder, fumitory, groundsel, hempnettle, knawel, spurge, spurry, emex, jungle rice, pondweed, dogfennel, carpetweed, bedstraw, ducksalad, naiad, cheatgrass, fall panicum, witchgrass, switchgrass, watergrass, teaweed, wild turnip, and sprangletop; biennials such as wild carrot, matricaria, wild barley, campion, chamomile, burdock, mullein, roundleaved mallow, bull thistle, houndstongue, moth mullein, and purple star thistle; or perennials such as white cockle, perennial ryegrass, quackgrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cat-tail wintercress, horsenettle, nutsedge, milkweed, and sicklepod.

Weeds of the genera against which the compounds of the invention are most effective (preemergence) are: Datura, Brassica, Setaria, Digitaria, Sorghum, Sesbania, Abutilon, Ipomea, and Echinochloa. Weed species against which the compounds of the invention are most effective (preemergence) are: *Datura stramonium* (jimsonweed), *Brassica kaber* (wild mustard), *Sorghum halepense* (johnsongrass), *Digitaria sanguinalis* (crabgrass), *Setaria glauca* (yellow foxtail), *Sesbania* spp. (coffeeweed), *Abutilon theophrasti* (velvetleaf), *Ipomea* spp. (wild morningglory), and *Echinochloa crusgalli* (barnyardgrass). When applied at very low rates, the weed species most effected are: *Brassica kaber* (wild mustard), *Digitaria sanguinalis* (crabgrass), *Abutilon theophrasti* (velvetleaf), *Sorghum halepense* (johnsongrass), *Setaria glauca* (yellow foxtail), and *Ipomea* spp. (wild morningglory).

Weeds against which the compositions are most effective when applied postemergence are of the genera Datura and Brassica, especially the species *Datura stramonium* (jimsonweed) and *Brassica kaber* (wild mustard).

b. Description Of The Method Of Controlling Weeds

As used herein and in the claims, the method of controlling the weeds comprises contacting the weeds with a herbicidally effective amount of a composition represented by the general formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, but preferably before they emerge, with one or more of the compounds represented by general formula (I) described herein. The phrase "the herbicidally effective amount" refers to that amount required under the environmental conditions in order to effectively control, that is, have an injury rating of seven (7) or greater (described herein) by which the weeds are injured and are not able to recover from the application of the compound. These are readily ascertained by the simple herbicidal tests mentioned herein.

c. General Application Of The Compounds

For practical use of herbicides, the compounds of this invention are generally incorporated into herbicial formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust compositions.

In some cases, the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal formulation according to this invention is illustrated by the following example, in which the quantities are in parts by weight.

EXAMPLE II

Preparation Of A Dust

| Product of Example I | 10 |
|---|---|
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Use Of Compounds Alone Or In Mixtures

Although all of the compounds described herein and represented by the general formula described herein are useful as herbicides, some of these are preferred and are better for applications against weeds. In general, all of the compounds described herein may be used either alone or together in mixtures. When used in mixtures the amount or ratio of one compound to another may vary from 0.01 to 100. The amount to use ranges from 0.10 pounds per acre to 100 pounds per acre depending upon the conditions.

e. Manner Of Application Of The Compounds Of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulation and the purpose for which it is designed, but generally the herbicidal formulations will comprise from about 0.05 to about 95 percent by weight of the active compounds of this invention. In a preferred embodiment of this invention, the herbicidal formulations will comprise from about 5 to 75 percent by weight of the active compound. The formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples Of Other Pesticides And Herbicides For Combinations

The other herbicides, defoliants, desiccants, and plant growth inhibitors, with which the compounds of this invention can be used in the herbicidal formulations to control weeds, can include: chlorophenoxy herbicides; such as 2,4-D, 2,4,5-T, MCPA, MCPB, 4-(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloroal urea, chloroxuron, cycluron, fenuron, monuron, monuron TCA, diuron, linuron, monolinuron, neburon, buturon, trimeturon, and the like; symmetrical triazine herbicides such as simazine, chlorazine, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl) piperidine, and the like; chlorinated aliphatic acid herbicides such as TCA, dalapon, 2,3-dichloropropionic acid, 2,2,3-TPA, and the like; chlorinated benzoic acid and phenylacetic acid herbicides such as 2,3,6-TBA, 2,3,5,6-TBA, dicamba, tricamba, amiben, fenac, PBA, 2-methoxy-3,5-dichlorophenylacetic acid, 3-methoxy-2,6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazide, phenyl mercuric acetate, endothal, biuret, technical chlordane, dimethyl 2,3,5,6-tetrachloroterephthalate, diquate, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EPEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular parent compounds.

g. Examples of Herbicidal Control

The following examples illustrate the utility of the compositions described herein for the control of weeds, particularly preemergence control.

These tests described herein were conducted in a laboratory under laboratory conditions according to standardized plant testing procedures. The soil mixture of 3:1:1 by volume of pulverized silt loam soil, washed sand, vermiculite mixture of pH 5.8 was adjusted to pH of 6.5 with agricultural lime and fertilized with 12-12-12 farm grade fertilizer at a rate of 10 pounds per acre of total nitrogen (110 kilograms/hectare). The soil mixture was placed in 3½ square inch Rib-Plastics pots #S-350 (to a depth of about 2.5 inches) and seeds were then planted. The number of seeds seeded depended upon their size, germination rate, and size of the plant. Generally sufficient seed was introduced to yield from 10 to 20 plants per pot under normal growth conditions. The seeds were then covered with from 0.2 to 0.25 inch of sand. For the postemergence test, the seeds were planted according to a time schedule which insured at the time of testing that the plants had the proper height and physiological development; that is at least one true leaf for broadleaf plants and three leaves for grasses at the time of spraying.

For the preemergence tests, the pots were sprayed with the test compound 1-2 hours after planting the seeds. For the postemergence test, the pots were sprayed when the plants had the proper physiological development as described above.

The test compounds were applied in the form of a spray, at a rate of 50 gallons per surface acre of soil. The pots of seeds (pre-emergence tests) were loaded into separate carrying trays (carrying only pots for preemergence testing) and the trays were loaded onto a conveyor belt which traveled at about 0.0625 miles per hour through a spraying unit equipped with a Tee-Jet 8001-E nozzle tip. As the tray passes into and out of the spraying unit, it trips solenoid valves which activate and deactivate the sprayer. The sprayer operated at 40 pounds per square inch of pressure, with compressed air. At the 10 pound per acre treatment, a total spray area of 5.78 square feet was treated with 600 milligrams of the test compound in 25 milliliters of solvent. Atrazine-80 W at 1.0 pound per acre was used as an internal check on the reproducibility of the tests.

Immediately after the spray treatment, the pots containing the preemergent test plants were watered with a gentle surface spray to more evenly distribute the test compound throughout the pot, and were then transferred to the greenhouse. The postemergence treating plants were immediately transferred to the greenhouse. The treated test plants were grown under GRO-LUX fluorescent lights, with an 18 hour photoperiod at a temperature of 80°±5° F. and a relative humidity of 50±10 percent. The treated pots were observed daily for interim response. The final observations, unless otherwise indicated, were made approximately 14 days or 21 days after treatment.

Observations included all abnormal physiological response of stem bending, petiole curvature, epinasty, hyponasty, retardation, stimulation, root development, chlorosis, necrosis, and related growth regulant characteristics. Observations were recorded on injury ratings, based on a scale of zero (0) which indicates no injury, to ten (10) which indicates complete kill, that is all plants and all replicates were dead. The intermediate numbers include the following: one (1)—trace injury; two and three (2 and 3)—a slight injury from which the plants recover with no reduction in growth; four, five, or six (4, 5, or 6)—moderate injury, plants recover but with reduced growth; seven and eight (7 and 8)—moderately severe injury, plants are stunted and may grow to maturity; nine and ten (9 and 10)—severe, plants do not recover from the injury.

Note, those values from 7–10 are indicative of the suitability of the compound at the application rate for herbicidal control of weeds, and are indicated in the tables described herein.

For the tests described herein, the test compound was dissolved in a standard solvent mixture of acetone, methanol, dimethylformamide, 90:8:2 volume per volume (v/v) for the pre-selected application rate. The weed species used in the preemergence tests described herein in which the control rating was 7 or higher were JMWD—jimsonweed (*Datura stramonium*), MSTD—wild mustard (*Brassica kaber*), YLFX—yellow foxtail (*Setaria glauca*), CBGS—crabgrass (*Digitaria sanguinalis*), JNGS—johnsongrass (*Sorghum halepense*), COFE—coffeeweed (*Sesbania* spp.), VTLF—velvetleaf (*Abutilon theophrasti*), MNGY—wild morningglory (*Ipomea* spp.), and BNGS—barnyardgrass (*Echinochloa crusgalli*).

The herbicidal test results are given in the following Tables. Column 1 of the Tables gives the weed species and Column 2 gives the numerical rating. Note, only ratings of 7 or higher are reported. In some cases, the rating results after 20 or more days of observation are in parentheses.

TABLE I

HERBICIDAL ACTIVITY AGAINST WEEDS PREEMERGENCE APPLICATION RATE AT 10 POUNDS PER ACRE USING ETHYL N—3,5-DICHLOROBENZOYL-N—ISOPROPYLAMINOACETATE PREPARED IN EXAMPLE I

| Weed | Numerical Rating |
|---|---|
| JMWD | 10 |
|  | (10)* |
| MSTD | 10 |
|  | (10)* |
| YLFX | 10 |
|  | (10)* |
| CBGS | 10 |
|  | (10)* |
| JNGS | 10 |
|  | (10)* |
| COFE | 10 |
|  | (10)* |
| VTLF | 10 |
|  | (10)* |
| MNGY | 10 |
|  | (10)* |
| BNGS | 10 |
|  | (10)* |

*Rating determined at 20 days

TABLE II

HERBICIDAL ACTIVITY AGAINST WEEDS AT POSTEMERGENCE APPLICATION RATE OF 10 POUNDS PER ACRE USING ETHYL N—3,5-DICHLOROBENZOYL-N—ISOPROPYLAMINOACETATE PREPARED IN EXAMPLE I

| Weed | Numerical Rating 14 days |
|---|---|
| COFE | 8 |
| BNGS | 9 |
| MSTD | 9 |
| MNGY | 7 |

When tested preemergence at lower rates of application, ethyl N-(3,5-dichlorobenzoyl)-N-isopropylaminoacetate was effective against JMWD, MSTD, YLFX, CBGS, JNGS, COFE, VTLF, MNGY, and BNGS at five (5) pounds per acre and was effective against MSTD, YLFX, CBGS, JNGS, VTLF, and MNGY at two (2) pounds per acre.

While the invention has been described with reference to specific details of certain illustrative embodiments, it is not intended that it shall be limited thereby except insofar as such details appear in the accompanying claims.

I claim:

1. A compound graphically represented by the general formula:

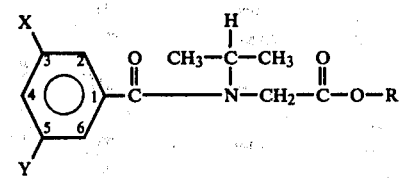

wherein:
X is chlorine, or bromine;
Y is hydrogen, chlorine, or bromine; and
R is an alkyl of up to four carbon atoms.

2. The compound as recited in claim 1, wherein R is an alkyl selected from the group consisting of methyl, ethyl, n-propyl, and isopropyl.

3. The compound as recited in claim 1, wherein R is ethyl.

4. The compound as recited in any of claims 1 through 3, wherein X is chlorine and Y is hydrogen.

5. The compound as recited in any of claims 1 through 3, wherein X and Y are bromine.

6. The compound as recited in any of claims 1 through 3, wherein X is bromine and Y is chlorine.

7. The compound as recited in claim 1, wherein X and Y are chlorine.

8. Ethyl N-(3,5-dichlorobenzoyl)-N-isopropylaminoacetate.

* * * * *